United States Patent [19]

Reiter née Eszes et al.

[11] Patent Number: 5,439,940
[45] Date of Patent: Aug. 8, 1995

[54] BENZ[E]INDENE DERIVATIVES

[75] Inventors: Klára Reiter née Eszes; Zoltán Budai; Tibor Mezei; Gábor Blaskó; Gyula Simig; István Gyertyán; Lujza Petöcz; Márton Fekete; Katalin Szemerédi; István Gacsályi; Gábor Gigler; Ludmilla Rohács née Zamkovaja; Mária Szécsey née Hegedüs; Enikö Szirt née Kiszelly, all of Budapest, Hungary

[73] Assignee: EGIS Gyogyszergyar Rt., Budapest, Hungary

[21] Appl. No.: 141,954

[22] Filed: Oct. 28, 1993

[30] Foreign Application Priority Data

Oct. 30, 1992 [HU] Hungary ............... P9203406

[51] Int. Cl.⁶ ............... A61K 31/15; C07C 251/58; C07C 251/54
[52] U.S. Cl. ............... 514/640; 514/212; 514/252; 514/255; 514/325; 514/357; 514/417; 514/427; 514/475; 540/610; 544/360; 544/380; 546/232; 546/285; 548/454; 548/561; 549/551; 564/257
[58] Field of Search ............... 514/640, 312, 252, 255, 514/325, 357, 417, 427, 475; 564/257; 540/610; 544/360, 380; 546/232, 285; 548/454, 561; 549/551

[56] References Cited

U.S. PATENT DOCUMENTS

| | | | |
|---|---|---|---|
| 3,429,919 | 2/1969 | Koopman et al. | 260/564 |
| 4,038,317 | 7/1977 | Wermuth et al. | 260/566 AE |
| 4,285,942 | 8/1981 | Budai et al. | 424/248.56 |
| 4,388,469 | 6/1983 | Ono et al. | 549/59 |

*Primary Examiner*—Peter O'Sullivan
*Attorney, Agent, or Firm*—Beveridge, DeGrandi, Weilacher & Young

[57] ABSTRACT

The invention relates to novel, pharmaceutically active benz[e]indene derivatives, a process for the preparation thereof, pharmaceutical compositions comprising the same, further to the use of the said benz[e]indene derivatives in the treatment of certain diseases and in the preparation of pharmaceutical compositions suitable for the treatment of said diseases.

The new benz[e]indene derivatives according to the invention correspond to the general formula

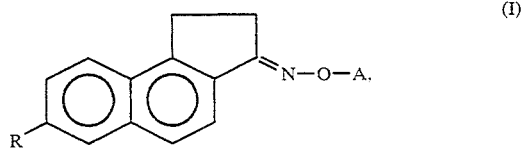

(I)

wherein

A represents a group of the formula alk-NR¹R², wherein alk represents a $C_{2-7}$ alkylene group optionally carrying a hydroxy substituent, $R^1$ and $R^2$ are independently hydrogen, $C_{1-7}$ alkyl, $C_{2-7}$ alkenyl, $C_{2-7}$ alkynyl, mono($C_{1-7}$)alkylamino($C_{1-7}$)alkyl, di($C_{1-7}$)alkylamino($C_{1-7}$)alkyl or $C_{3-7}$ cycloalkyl; or $R^1$ and $R^2$ together with the nitrogen atom to which they are attached form a 4 to 7 membered ring, optionally comprising an oxygen atom or a further nitrogen atom, which latter may carry a phenyl, benzyl, pyridyl, pyrimidinyl or $C_{1-3}$ alkyl substituent which substituents may, in turn, bear a hydroxy or methoxy group or a halogen atom or a halophenyl group; or $R^1$ and $R^2$ together with the nitrogen atom to which they are attached form a phthalimido group; or A represents pyrimidino, 2,3-epoxypropyl or a group of the formula —C(O)NHR³, wherein $R^3$ stands for $C_{1-7}$ alkyl, $C_{2-7}$ alkenyl or $C_{3-8}$ cycloalkyl; and R denotes hydrogen or $C_{1-7}$ alkyl, stereoisomers and optically active isomers and the possible mixtures thereof, further acid addition salts and quaternary ammonium derivatives of these compounds.

3 Claims, No Drawings

BENZ[E]INDENE DERIVATIVES

The present invention relates to novel, pharmaceutically active benz[e]indene derivatives, a process for the preparation thereof, pharmaceutical compositions comprising the same, further to the use of the said benz[e]indene derivatives in the treatment of certain diseases and in the preparation of pharmaceutical compositions suitable for the treatment of said diseases.

According to an aspect of the present invention there are provided new benz[e]indene derivatives of the formula

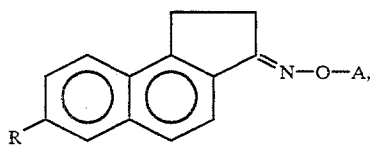
(I)

wherein
A represents a group of the formula alk-NR$^1$R$^2$ wherein alk represents a C$_{2-7}$ alkylene group optionally carrying a hydroxy substituent,
  R$^1$ and R$^2$ are independently hydrogen, C$_{1-7}$ alkyl, C$_{2-7}$ alkenyl, C$_{2-7}$ alkynyl, mono(C$_{1-7}$)alkylamino(C$_{1-7}$)alkyl, di(C$_{1-7}$)alkylamino(C$_{1-7}$)alkyl or C$_{3-7}$ cycloalkyl; or
  R$^1$ and R$^2$ together with the nitrogen atom to which they are attached form a 4 to 7 membered ring, optionally comprising an oxygen atom or a further nitrogen atom, which latter may carry a phenyl, benzyl, pyridyl, pyrimidinyl or C$_{1-3}$ alkyl substituent which substituents may, in turn, bear a hydroxy or methoxy group or a halogen atom or a halophenyl group; or
  R$^1$ and R$^2$ together with the nitrogen atom to which they are attached form a phthalimido group; or
A represents pyrimidino, 2,3-epoxypropyl or a group of the formula —C(O)NHR$^3$, wherein
  R$^3$ stands for C$_{1-7}$ alkyl, C$_{2-7}$ alkenyl or C$_{3-8}$ cycloalkyl; and
R denotes hydrogen or C$_{1-7}$ alkyl,
stereoisomers and optically active isomers and the possible mixtures thereof, further acid addition salts and quaternary ammonium derivatives of these compounds.

The compounds according to the present invention possess valuable tranquillo-sedative, anticonvulsive, analgesic, antianginal, local anaesthetic and antiinflammatory effects.

The term "alkyl group" used throughout the specification relates to straight or branched chained saturated aliphatic hydrocarbon groups having the given number of carbon atom(s), e.g. methyl, ethyl, propyl, isopropyl, n-butyl, tert-butyl etc. The term "alkenyl group" relates to straight or branched chained alkenyl groups containing the given number of carbon atoms, e.g. vinyl, allyl, 2-methylallyl, 1-propenyl, 1-butenyl, 2-butenyl, 2-hexenyl etc. The term "alkynyl group" covers straight or branched chain aliphatic hydrocarbon groups comprising at least one triple bond (e.g. propargyl etc.). The term "C$_{3-7}$ cycloalkyl" relates to cycloalkyl groups Such as cyclopropyl, cyclobutyl, cyclopentyl, cyclohexyl etc. As "4 to 7 membered ring" aromatic or partially or completely saturated heterocyclic rings are mentioned, which contain as heteroatom a nitrogen atom and optionally an oxygen atom or a further nitrogen atom (e.g. piperidyl, morpholinyl, piperazinyl, imidazolyl, pyrimidinyl, pyrazolyl, imidazolinyl, pyrrolidinyl etc.) and the latter heteroatom may carry a phenyl, benzyl, pyridyl, pyrimidinyl, or a C$_{1-3}$ alkyl substituent which substituents may, in turn, bear a hydroxy or methoxy group or a halogen atom. The term "halogen atom" encompasses all the four halogen atoms (fluorine, chlorine, bromine and iodine).

The structurally closest prior art compounds possess antiviral or antiinflammatory effects [Il. Farmaco.-Ed. Sc. 30, 568–580 (1975); Arch. Pharm. (Weinheim) 316, 309–315 (1983)].

According to another aspect of the present invention there is provided a process for the preparation of benz[e]indene derivatives of the formula

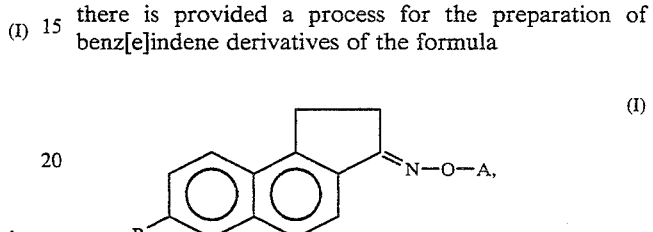
(I)

stereoisomers and optically active isomers and the possible mixtures thereof, further the acid addition salts and quaternary ammonium derivatives of these compounds, which comprises
  a) reacting a benz[e]indene derivative of the formula

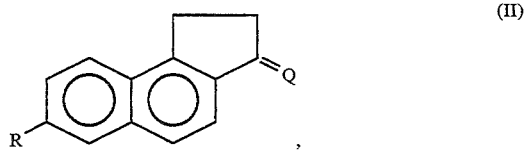
(II)

wherein Q represents a group of the formula =N—OH and R is as stated above, with a halo compound of the formula

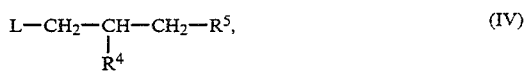
(IV)

wherein L stands for halogen and R$^4$ and R$^5$ together represent oxygen, in the presence of a basic condensing agent in order to prepare a compound of the formula (I), wherein A stands for 2,3-epoxypropyl; or
  b) for the preparation of compounds of the formula (I), wherein A denotes a group of the formula alk-NR$^1$R$^2$, wherein alk, R$^1$ and R$^2$ are as stated above,
  b$_1$) reacting a benz[e]indene derivative of the formula (II) or acid addition salts thereof, wherein Q stands for a group of the formula =N—OH and R is as stated above, with a halo compound of the formula

(III)

wherein alk, R$^1$ and R$^2$ are as stated above and L stands for halogen, or with an acid addition salt thereof in the presence of a basic condensing agent; or b2) reacting a compound of the formula (I), wherein A stands for 2,3-epoxypropyl, with an amine of the formula

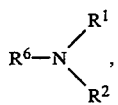  (V)

wherein $R^1$ and $R^2$ are as stated above and $R^6$ denotes hydrogen; or b3) reacting a benz[e]indene derivative of the formula (II), wherein Q stands for oxygen or sulfur and R is as stated above, with a compound of the formula (III), wherein alk, $R^1$ and $R^2$ are as stated above and L represents a group of the formula $H_2N$—O—, or with an acid addition salt thereof in the presence of a basic condensing agent; or c) reacting a benz[e]indene derivative of the formula (II), wherein Q-represents a group of the formula =N—OH and R is as stated above, with a halopyrimidine of the formula

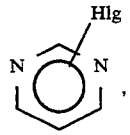  (VII)

wherein Hlg represents halogen, in the presence of a basic condensing agent in order to prepare a compound of the formula (I), wherein A stands for a pyrimidino group; or d) reacting a benz[e]indene derivative of the formula (II), wherein Q is a group of the formula =N—OH and R is as stated above, with an isocyanate of the formula

 $R^3$—NCO  (VI), wherein $R^3$ is as stated above, in order to prepare a compound of the formula (I), wherein A stands for a group of the formula —C(O)$NHR^3$, and, if desired, converting a compound of the formula (I) thus obtained into a pharmaceutically acceptable acid addition salt or quaternary ammonium derivative, or liberating a free base of the formula (I) from a salt thereof and/or separating the stereoisomers and/or optically active isomers.

According to variant a) of the process of invention compounds of the formula (I) containing a 2,3-epoxypropyl group in the place of A are prepared by reacting a compound of the formula (II), wherein Q stands for a group of the formula =N—OH, with a compound of the formula (IV), wherein L represents halogen and $R^4$ and $R^5$ together form oxygen. The reaction is carried out in the presence of a basic condensing agent. For this purpose preferably an alkali metal hydride or alkali metal amide is used. It is preferable to use the appropriate sodium compounds, but potassium hydride or potassium amide can also be applied. The reaction is carried out in an inert aprotic solvent, preferably in a dipolar aprotic or an apolar aprotic solvent, such as dimethyl formamide, dimethyl sulfoxide, acetonitrile, acetone, benzene or homologues thereof or mixtures of such solvents. The reaction temperature may vary between 0° C. and 120° C., but it is preferable to carry out the reaction between 40° C. and 50° C.

According to variant b) of the process of invention compounds of the formula (I) containing a group of the formula alk-$NR^1R^2$ in the place of A are prepared. For this purpose according to variant b1) a benz[e]indene derivative of the formula (II), wherein Q represents a group of the formula =N—OH, is reacted with a halo compound of the formula (III) or with an acid addition salt thereof, in the presence of a basic condensing agent. As basic condensing agent an alkali metal hydride, alkali metal amide, alkali metal hydroxide or mixtures thereof can be used. If an alkali metal hydride or amide is applied, the reaction is carried out in an aprotic solvent, preferably dipolar aprotic or apolar aprotic solvent (e.g. dimethyl formamide, dimethyl sulfoxide, acetonitrile, acetone, benzene or homologues thereof or mixtures of such solvents). If an alkali metal hydroxide is used as basic condensing agent, the reaction is carried out in a protic or dipolar aprotic solvent, preferably in water, an aliphatic alcohol, dimethyl formamide, dimethyl sulfoxide or mixtures thereof. The reaction temperature may be varied between 0° C. and 120° C. but it is preferable to carry out the reaction between 40° C. and 50° C.

According to variant b2) of the process of the invention a compound of the formula (I) containing a 2,3-epoxypropyl group in the place of A is reacted with an amine of the formula (V). The reaction is generally carried out in a protic solvent, preferably in an aliphatic alcohol, at a temperature between 0° C. and 120° C., but it can also be performed without using any solvent. In the latter case the reaction is carried out in a closed vessel, at an elevated temperature, preferably at 50° to 100° C. The thus-obtained compounds of the formula (I) can be isolated from the reaction mixture by methods known per se, e.g. by distilling off the solvent and crystallizing the residue or subjecting it to fractional distillation in vacuo.

According to variant b3) of the process of invention a compound of the formula (II) containing oxygen or sulfur in the place of Q is reacted with a compound of the formula (III), wherein L represents a group of the formula $H_2N$—O, or with an acid addition salt thereof, in the presence of a basic condensing agent. As basic condensing agent an organic base (e.g. pyridine, piperidine or morpholine) is used. The reaction is carried out in a protic or dipolar aprotic solvent. As protic solvent preferably aliphatic alcohols, as dipolar aprotic solvent preferably dimethyl formamide or dimethyl acetamide is used. The reaction is carried out at a temperature between 0° C. and 120° C., preferably between 70° C. and 100° C. The thus-obtained compound of the formula (I) is isolated from the reaction mixture by methods known per se, e.g. by evaporating the solvent.

According to variant c) of the process of invention compounds of the formula (I) containing a pyrimidino group in the place of A are prepared by reacting a compound of the formula (II), wherein Q is a group of the formula =N—OH, with a halopyrimidine of the formula (VII). The reaction is carried out in the presence of a basic condensing agent. For this purpose preferably an alkali metal amide or alkali metal hydride is used. The reaction is carried out in an inert solvent, e.g. in an ether (such as tetrahydrofurane or dibutyl ether), benzene or a homologue thereof. The reaction temperature may be varied between 30° C. and 140° C., but it is preferable to carry out the reaction between 50° C. and 100° C.

According to variant d) of the process of the invention compounds of the formula (I) containing a group of the formula —C(O)NHR$^3$ in the place of A are prepared by reacting a benz[e]indene derivative of the formula (II), wherein Q represents a group of the formula =N—OH, with an isocyanate of the formula (VI). The reaction is carried out in an apolar aprotic solvent, preferably in benzene or in a homologue thereof, dichloromethane, 1,2-dichloroethane, chloroform or in mixtures thereof. The reaction temperature may vary between 0° C. and 80° C., but it is preferable to carry out the reaction at 15° to 30° C. The thus-obtained compounds of the formula (I) can be isolated from the reaction mixture by methods known per se, e.g. by evaporating the solvent.

The benz[e]indene derivatives of the formula (II) containing a group of the formula =N—OH in the place of Q used as starting substances for the process according to the invention can be prepared by the methods described in J. Chem. Soc. 1952, 3605–3607 or ibid. 1958, 2437–2440. The benz[e]indene derivatives of the formula (II) containing oxygen or sulfur in the place of Q can be prepared as described in J. Chem. Soc. 1958, 10800–4.

The compounds of the formula (III) can be prepared e.g. according to the method specified in the Hungarian patent specification No. 201,324 or in J. Pharm. Sci. 58, 138–141 (1969).

The amines of the formula (V), the isocyanates of the formula (VI) and the halopyrimidines of the formula (VII) are commercial products or can be prepared by methods known per se.

The compounds of the formula (I) according to the present invention possess valuable tranquillo-sedative, anti-convulsive, analgesic, antianginal, local anaesthetic and antiinflammatory effects. At the same time they are only slightly toxic.

The biological activity of the new compounds according to the invention is shown by the following tests:

I. Acute Toxicity

Mice belonging to the NMRI strain (body weight 20–25 g, both male and female) were used, 6 to 10 animals for each dose. The test compound was administered orally in a volume of 20 ml/kg. The applied maximal dose was 1000 mg/kg. After the treatment the animals were observed for a period of 7 days. The mice were kept in a plastic cage at room temperature. The animals got tap water and standard mouse fodder ad libitum. The toxicity data were determined by the aid of the method of Litchfield and Wilcoxon [Litchfield, J. T., Wilcoxon, F. W.: J. Pharmacol. Exp. Ther., 96, 99 (1949)]. The results are summarized in Table 1.

TABLE 1

| Acute toxicity on mice | | | |
|---|---|---|---|
| Example No. | LD$_{50}$ (mg/kg) | Example No. | LD$_{50}$ (mg/kg) |
| 4 | 600 | 8 | >1000 |
| 7 | 700 | 22 | >1000 |
| 3 | 640 | 9 | 320 |
| 11 | >1000 | 18 | >1000 |
| 1 | 820 | 19 | >1000 |
| 12 | >1000 | 17 | 660 |
| Chlor-promazine | 315 | Thioridazine | between 360 and 685* |
| Chlordi- | 650 | Meprobamate | 1350 |

TABLE 1-continued

| Acute toxicity on mice | | | |
|---|---|---|---|
| Example No. | LD$_{50}$ (mg/kg) | Example No. | LD$_{50}$ (mg/kg) |
| azepoxide | | | |

*data given in the literature

2. Tranquillo-Sedative Effect

The hexobarbital narcosis potentiating effect was examined on mice. Groups consisting of 6 animals were used for each dose. The animals were treated orally with the test compound, whereby sleeping was induced 1 hour later by administering a 40 mg/kg i.v. dose of hexobarbital both to the test and control groups. The animals which had a sleeping time more than 2.5 times longer than the control group were considered to show a positive reaction. ED$_{50}$ values were calculated from the thus-transformed data [Kaergaard Nielsen C. et al., Arch. Int. Pharmacodyn. 2, 170 (1967)]. The results are summarized in Table 2.

TABLE 2

| Hexobarbital narcosis on mice | |
|---|---|
| Test compound (Example No.) | ED$_{50}$ (mg/kg) (or effect observed in the given dose) |
| 1 | 200 (100%) |
| 12 | 200 (83%) |
| 8 | 100 (67%) |
| 19 | 67 |
| 17 | 11 |
| Meprobamate | 260 |

The spontaneous motility inhibiting activity was examined according to the method of Borsy et al. Groups consisting of 3 mice each were treated orally with different doses of the compounds to be tested, then the test animals were placed in a Dews equipment. In this equipment the number of interruptions of infrared beam within 30 minutes was counted. From these data 50% inhibiting doses (ID$_{50}$) were determined by the aid of a line of regression. [Borsy, J., Csányi, E., Lázár, I.: Arch. Int.. Pharmacodyn. 124, 1 (1960)]. The data are summarized in Table 3.

TABLE 3

| Motility inhibiting activity | |
|---|---|
| Test compound (Example No.) | ID$_{50}$ (mg/kg) |
| 12 | about 100 |
| 19 | 43 |
| 17 | 6 |
| Meprobamate | 232 |

The compound of Example 17, the most active member in the structural group, was examined in detail for tranquillizing and sedative effects to establish whether the supposed human therapeutic activity of the compound would be of antipsychotic or of anxiolytic character.

II. A. Antipsychotic Effect

The antipsychotic (neuroleptic) effect was measured by the inhibition of the learned conditioned avoidance reflex. The male Wistar rats used for the study were of 120–150 g bodyweight at the commencement of learning. A shuttle box was used as experimental device; it consisted of two parts, 24×24.5×23 cm each, separated by a wall with a 6×9 cm gate. In response to a suitable warning stimulus, in order to avoid the punishing (unconditioned) stimulus, animals within the box passed through the gate from one part over the other. The warning, i.e. conditioned stimulus (CS), a white light (1 Hz) blinking for 15 seconds, was applied at the place of the actual animal existence. The unconditioned stimulus (US), in form of 0.6 mA intensity electric shock, was randomly applied to the paw during the last 5 seconds of the conditioned stimulus. Animal's movement during the CS and US from one part of the box over the other, was defined as avoidance and escape responses, respectively. Both responses ceased the actual stimulus and stopped the trial. The time elapsed until the next trial (intertrial interval, ITI) was 15 seconds. While one experiment was carried out daily, an experiment consisted of 80 trials. Learning efficiency was expressed as percentage of the successful to the total avoidances. Effect of the neuroleptic drugs was examined in animals with stabilized conditioned reflexes and with at least 75% learning efficiency. Dosing was carried out once a week, one hour before the measurement in the shuttle box. To calculate the neuroleptic effect (50% inhibiting dose, ID$_{50}$), results obtained after the treatment were compared to those obtained on the previous day (controls).

The extrapyramidal syndrome, the most important side effect limiting the application of the neuroleptic drugs in man, can be produced in experimental animals in the form of catalepsy. Our experiments in 150-160 g Wistar rats were performed according to Morpurgo. The catalepsy, appearing 60 minutes after dosing, was scored as follows. Both forelegs of each animal were put for 10 seconds onto a rubber stopper of 3 cm height, then for additional 10 seconds onto a same stopper of 9 cm height. 0.5 and 1 scores per foot (a total of maximum 3 scores) were given if animals failed to return their feet within 10 seconds from the lower and higher stoppers, respectively. The procedure was repeated in each 30 minutes during four hours, obtaining scores proportional to the degree of the catalepsy. Results were used to calculate the minimum effective dose [MED, the lowest dose resulting statistically significant alteration, c.f.: Morpurgo, C.: Arch. Int. Pharmacodyn., 137, 87 (1962)]. The data thus obtained are summarized in Table 4.

TABLE 4

| Test compound (Example No.) | Antipsychotic effect on rat | | |
|---|---|---|---|
| | Conditioned reflex ID$_{50}$ (mg/kg) | Catalepsy [MED (mg/kg)] | Therapeutic index* |
| 17 | 26.3 | 100 | 3.8 |
| Chlorpromazine | 13.2 | 20 | 1.5 |
| Thioridazine | 108 | 80 | 0.7 |

*Catalepsy MED

Conditioned Reflex ID$_{50}$

From the data of the above Table it can be seen that the compound of Example 17 is superior to Thioridazine and inferior to Chlorpromazine considering the antipsychotic effect, but it is superior to both reference substances in respect of the dose ratio of the corresponding side and main effects. Consequently a more favourable safety can be expected in patients treated with the compound of Example 17.

II. B. Anxiolytic Effect

The anxiolytic effect was tested by using the method of Vogel et al. Male Wistar rats of 160-180 g bodyweight were kept free of food and drinking water for 24 and 48 hours, respectively. Test and carrier substances were administered intraperitoneally two hours before testing. Animals within the experimental chamber were provided with drinking water through an inserted tube. After the animals' each twenty lapping for water the device emitted a 2 mA intensity electric shock through the drinking tube. During 5 minutes the shocks tolerated by the animals in order to quench their thirst were counted. The effect of treatment was expressed as the % increase of the tolerated shocks. The minimum effective dose (MED) was determined for each test compound [Voqel, J. R., Beer, B., Clody, D. E.: Psychopharmacologia (Berl.) 21, 1 (1971)]. The data thus obtained are summarized in Table 5.

TABLE 5

| Anxiolytic effect on rat | |
|---|---|
| Test compound (Example No.) | MED (mg/kg) |
| 17 | 0.1 |
| Chlordiazepoxide | 2.5 |
| Meprobamate | 25 |

From the above Table it can be seen that the compound of Example 17 is superior to the reference substances by orders of magnitude.

Thus, it can be established that the compound of Example 17 has, when administered in higher doses, a neuroleptic, while in case of smaller doses an anxiolytic character.

III. Anticonvulsive Activity

The pentetrazole spasm inhibiting test was performed according to the modified method of Benziger and Hans. Groups of mice consisting of 6 animals each, belonging to the NMRI strain (body weight: 20-25 g), were treated orally with the compound to be tested and the vehicle without active agent, respectively. 1 hour after the treatment a dosage of 125 mg/kg of pentetrazole was administered to each animal, intraperitoneally, and the tonic spasm of the lower limb extensor was recorded [Benziger, R., Hans, D.: Arch. Int. Pharmacodyn., 167, 245 (1967)].

The inhibition of nicotine spasm and lethality was examined on mice according to the method of Stone. One hour after the oral treatment a dosage of 1.4 mg/kg of nicotine is injected intravenously, and the spasm developed as well as the lethality within 1 hour were recorded at both the test and control groups. [Stone, C. C., Mecklenburg, K. L., Torchiana, M. L.: Arch. Int. Pharmacodyn., 117, 419 (1958)].

The ED$_{50}$ values were determined according to the method of Litchfield and Wilcoxon. The results are shown in Table 6.

TABLE 6

| Anticonvulsive activity on mice | | |
|---|---|---|
| Test compound (Example No.) | Inhibition of pentetrazole spasm, ED$_{50}$ (mg/kg) | Inhibition of nicotine spasm, ED$_{50}$ (mg/kg) |
| 4 | — | 4 |
| 3 | 96 | 29 |
| 11 | 84 | — |
| 12 | 30 | — |

TABLE 6-continued

| | Anticonvulsive activity on mice | |
|---|---|---|
| Test compound (Example No.) | Inhibition of pentetrazole spasm, $ED_{50}$ (mg/kg) | Inhibition of nicotine spasm, $ED_{50}$ (mg/kg) |
| Trimethadione | 400 | — |
| Trihexyphenidyl | — | 20 |

IV. Analgesic Effect

The test was carried out on mice, weighing 20–25 g, belonging to the NMRI strain according to the method of Newbould 0.75% acetic acid is administered to the animals in a volume of 20 ml/kg one hour after the treatment with the test compounds and vehicles, respectively. The characteristic "writhing reactions" were counted for a period of 5 minutes, starting from the fifth minute after challenge. The number of writhing was observed for both the treated and the control group. Each group of animals consisted of at least 10 mice. The 50% inhibition doses ($ID_{50}$) were determined with the aid of a line of regression [Newbould, B. B.: Brit. J. Pharmacol., 35, 487 (1969)]. The results are disclosed in Table 7.

TABLE 7

| Analgesic effect on mice | |
|---|---|
| Test compound (Example No.) | $ID_{50}$ (mg/kg) |
| 19 | 65 |
| 17 | 14 |
| Acetylsalicylic acid | 261 |
| Paracetamol | 421 |

V. Antianginal Effect

The test was carried out on male rats weighing 180–220 g. The animals were narcotized with the aid of chloralose-urethane. ECG was registered by means of needle electrodes in standard II output. Antianginal effect was tested according to the method of Nieschultz. Experimental coronary insufficiency was induced by administering glanduitrine (4 NE/kg i.v.). The magnitude of the T-wave before and after the administration of glanduitrine was measured in the treated and control groups [Nieschultz, E., Popendiker, K., Hoffmann, I.: Arzneim.-Forsch., 5, 680 (1955)]. The results are summarized in Table 8.

TABLE 8

| Antianginal effect on rat | | |
|---|---|---|
| Test compound (Example No.) | Inhibition in a dose of 2 mg/kg | $ED_{50}$ (mg/kg) |
| 4 | 100% | 0.19 |
| 11 | 54% | |
| 12 | 56% | |
| 8 | 56% | |
| 22 | 59% | |
| 18 | 59% | |
| 17 | 50% | |
| Prenylamine | 41% | 6.6 |

VI. Local Analgesic Effect

The test was carried out according to the method of Truant d'Amato. 0.2 ml of test material was injected around the nervus ischiadicus in the middle of femur with a needle of 1 cm length. The criterion of analgesic effect was the lack of the motoric control of foot muscles. The duration of effect was registered and the 50 percentile effective concentration ($EC_{50}$) was calculated on the basis of the dose-effect curve. Lidocain was used as reference substance Truant d'Amato, A. P., Wiedling, S.: Acta Chir. Scand., 116, 351 (1958)]. The results are disclosed in Table 9.

TABLE 9

| Local analgesic effect | |
|---|---|
| Test compound (Example No.) | $EC_{50}$ (%) |
| 4 | 0.18 |
| 7 | 0.20 |
| 9 | 0.20 |
| Lidocain | 0.19 |

VII. Antiinflammatory Effect

The antiinflammatory effect was investigated on Wistar rats weighing 150–180 g according to the method of Winter et al. 0.1 ml of a 1 percent carrageen suspension was injected subcutaneously into the plantar region of one of the hind paws. The animals were fasted for 12 hours and received drinking water ad libitum. One hour before treatment with the test compound the rats were hydrated orally with 30 ml/kg of tap water. The test compounds and the vehicle were administered p.o. in a volume of 10 ml/kg, then 1 hour later carrageen was applied. The volume of the treated paw was measured by mercury-plethysmometer before and 3 hours after injection in such a way that displacement of the liquid arising from the volume alteration was indicated on a millimeter scale. The dose resulting in an inhibition of 30% ($ID_{30}$) was determined by the aid of a line of regression [Winter, C. A., Risley, E. A., Nuss, G. W.: Proc. Soc. Exp. Biol. Med., 111, 544 (1962)]. The results are summarized in Table 10.

TABLE 10

| Antiinflammatory effect on rat | |
|---|---|
| Test compound (Example No.) | $ID_{30}$ (mg/kg) |
| 17 | 40 |
| Acetylsalicylic acid | 62 |
| Paracetamol | 195 |

According to a further aspect of the present invention there are provided pharmaceutical compositions comprising as active ingredient at least one compound of the formula (I) or a pharmaceutically acceptable acid addition salt and/or quaternary ammonium derivative thereof, in admixture with suitable inert solid or liquid pharmaceutical carriers.

The pharmaceutical compositions of the present invention can be prepared by methods known per se by admixing the active ingredient with suitable inert solid or liquid carriers or diluents and bringing the mixture to galenic form.

According to a further aspect of the present invention there is provided the use of the compounds of the formula (I) or pharmaceutically acceptable salts and/or quaternary ammonium derivatives thereof in the preparation of pharmaceutical compositions having particularly tranquillo-sedative, anticonvulsive and antianginal effects.

According to a still further aspect of the present invention there is provided a method of tranquillo-sedative, anticonvulsive and antianginal treatment, which comprises administering to the patient an effective amount of a compound of the formula (I) or a pharmaceutically acceptable salt and/or quaternary ammonium derivative thereof.

The invention is further illustrated by the following Examples of non-limiting character.

EXAMPLE 1

3-[2-(N,N-Dimethylamino)-ethoxyimino]-2,3-dihydro-1H-benz[e]indene 2,3-Dihydro-1H-benz[e]inden-3-one oxime (19.72 g, 0.1 mole) is converted into a salt in a saturated (30–40%) aqueous solution of an alkali hydroxide (sodium hydroxide and/or potassium hydroxide) in the presence of dimethyl sulfoxide, and the salt thus obtained is reacted with 2-chloro-N,N-dimethylethylamine hydrochloride (15.85 g, 0.11 mole) at a temperature of 40°–50° C. The stirring is continued until the starting oxime cannot be detected in the reaction mixture by thin layer chromatography (Kieselgel 60 F254, ethanol:ammonium hydroxide=9:1). The reaction mixture is poured onto 600 g of icy water, the product is extracted with 400 cm$^3$ of benzene, the organic phase is washed with saturated aqueous sodium chloride solution and dried over anhydrous magnesium sulfate. The solvent is distilled off under reduced pressure and the product thus obtained is purified by extraction with n-hexane.

Yield: 19.03 g (70.9%) of oil

Hydrochloride (1/1), m.p.: 237°–241° C.

Analysis for the formula $C_{17}H_{21}ClN_2O$ (304.83): Calculated: C %=66.98, H %=6.94, Cl %=11.63, N %=9.19; Found: C %=66.81, H %=6.92, Cl %=11.56, N %=9.20.

UV: $\lambda_{max}$ = 242 nm ($\epsilon$ = 33922)
250 nm ($\epsilon$ = 44506)
260 nm ($\epsilon$ = 39153)

EXAMPLE 2

3-[3-(N,N-Dimethylamino)-propoxyimino]-2,3-dihydro-1H-benz[e]indene

One proceeds as specified in Example 1 except that instead of 2-chloro-N,N-dimethylethylamine hydrochloride 3-chloro-N,N-dimethylpropylamine hydrochloride (17.4 g, 0.11 mole) is used.

Yield: 22.42 g (74.9%) of oil

Hydrochloride (1/1), m.p.: 226°–228° C.

Analysis for the formula $C_{18}H_{23}ClN_2O$ (318.84): Calculated: C %=67 80, H %=7.27, Cl %=11.12, N %=8 78; Found: C %=67.69, H %=7.14, Cl %=11.15, N %=8.73.

UV: $\lambda_{max}$ = 253 nm ($\epsilon$ = 43799)
262 nm ($\epsilon$ = 38229)

EXAMPLE 3

3-[2-(N,N-Diethylamino)-ethoxyimino]-2,3-dihydro-1H-benz[e]indene

One proceeds as specified in Example 1 except that instead of 2-chloro-N,N-dimethylethylamine hydrochloride 2-chloro-N,N-diethylethlamine hydrochloride (18.93 g, 0.11 mole) is used.

Yield: 23.21 g (78.3%) of oil

Hydrochloride (1/1) M.p.: 207°–211° C..

Analysis for the formula $C_{19}H_{25}ClN_2O$ (332.87): Calculated: C %=68.55, H %=7.57, Cl %=10.65, N %=8.42; Found: C %=68.43, H %=7.65, Cl %=10.73, N %=8.35.

UV: $\lambda_{max}$ = 242 nm ($\epsilon$ = 33124)
254 nm ($\epsilon$ = 48731)
262 nm ($\epsilon$ = 38844)

EXAMPLE 4

3-[2-(N-1-Methylethyl-2-propylamino)-ethoxyimino]-2,3-dihydro-1H-benz[e]indene

One proceeds as specified in Example I except that instead of 2 -chloro-N, N-dimethylethylamine hydrochloride N-(2-chloroethyl)-N-(1-methylethyl)-2-propaneamine hydrochloride (22.02 g, 0.11 mole) is used.

Yield: 24.82 g (76.5%) of oil

Hydrochloride (1/1), m.p.: 190°–197° C.

Analysis for the formula $C_{21}H_{29}ClN_2O$ (360.92): Calculated: C %=69.88, H %=8.10, Cl %=9.82, N %=7.76; Found: C %=69.72, H %=8.24, Cl %=10.06, N %=7.61.

UV: $\lambda_{max}$ = 242 nm ($\epsilon$ = 32826)
253 nm ($\epsilon$ = 45125)
261 nm ($\epsilon$ = 40103)

EXAMPLE 5

(±)-3-[1-(N,N-Dimethylamino-2-methyl)-ethoxyimino]-2,3 -dihydro-1H-benz[e]indene One proceeds as specified in Example 1 except that instead of 2-chloro-N,N-dimethylethylamine hydrochloride 1-chloro-N,N-dimethyl-2-propaneamine (13.38 g, 0. 11 mole) is used.

Yield: 24.15 g (84.9%) of oil

Hydrochloride (1/1), m.p.: 234°–236° C.

Analysis for the formula $C_{18}H_{23}ClN_2O$ (318.84): Calculated: C %=67.80, H %=7.23, Cl %=11.12, N %=8.79; Found: C %=67.74, H %=7.18, Cl %=11.23, N %=8.67.

UV: $\lambda_{max}$ = 243 nm ($\epsilon$ = 35307)
252 nm ($\epsilon$ = 45796)
260 nm ($\epsilon$ = 40066)

EXAMPLE 6

3-[3-(2,N,N-Trimethylamino)-propoxyimino]-2,3-dihydro-1H-benz[e]indene

One proceeds as specified in Example 1 except that instead of 2-chloro-N,N-dimethylethylamine hydrochloride 3-chloro-2,N,N-trimethylpropylamine (14.92 g, 0.11 mole) is used.

Yield: 27.57 g (93.0%) of oil

Hydrochloride (1/1) M.p.: 194°–196 ° C. (isopropanol).

Analysis for the formula $C_{19}H_{25}ClN_2O$ (332.822): Calculated: C %=68.56, H %=7.57, Cl %=10.65, N %=8.41; Found: C %=68.41, H %=7.45, Cl %=10.68, N %=8.36.

UV: $\lambda_{max}$ = 243 nm ($\epsilon$ = 33070)
253 nm ($\epsilon$ = 42544)
262 nm ($\epsilon$ = 36457)

EXAMPLE 7

3-[2-(N-Pyrpolidinyl)-ethoxyimino]-2,3-dihydro-1H-benz[e]indene

One proceeds as specified in Example 1 except that instead of 2-chloro-N,N-dimethylethylamine hydrochloride N-(2-chloroethyl)-pyrrolidine hydrochloride (18.71 g, 0.11 mole) is used.

Yield: 20.95 g (71.2%), m.p.: 89°–92° C. (petrol)

Hydrochloride/ethanol (1/1/1), M.p.: 219°–227° C. (ethanol).

Analysis for the formula $C_{21}H_{29}ClN_2O_2$ (376.94): Calculated: C %=66.92, H %=7.76, Cl %=9.41, N %=7.43; Found: C %=66.90, H %=7.56, Cl %=9.37, N %=7.40.

UV: $\lambda_{max}$ = 252 nm ($\epsilon$ = 47042)
260 nm ($\epsilon$ = 41210)

EXAMPLE 8

3-[2-(N-Piperidinyl)-ethoxyimlno]-2,3-dihydro-1H-benz[e]indene

One proceeds as specified in Example 1 except that instead of 2-chloro-N,N-dimethylethylamine hydrochloride N-(2-chloroethyl)-piperidine hydrochloride (20.25 g, 0.11 mole) is used.

Yield: 27.14 g (88.0%) of oil

Hydrochloride (1/1) M.p.: 209°–214° C. (isopropanol).

Analysis for the formula $C_{20}H_{25}ClN_2O$ (344.89): Calculated: C %=69.65, H %=7.31, Cl %=10.28, N %=8.12; Found: C %=69.70, H %=7.28, Cl %=10.22, N %=8.02.

UV: $\lambda_{max}$ = 244 nm ($\epsilon$ = 34500)
252 nm ($\epsilon$ = 43988)
260 nm ($\epsilon$ = 37981)

EXAMPLE 9

3-[3-(N-Piperidinyl)-propoxyimino]-2,3-dihydro-1H-benz[e]indene

One proceeds as specified in Example 1 except that instead of 2-chloro-N,N-dimethylethylamine hydrochloride N-(3-chloropropyl)-piperidine hydrochloride (21.8 g, 0.11 mole) is used.

Yield: 26.28 g (81.5%)

Hydrochloride (1/1) M.p.: 205°–208° C.

Analysis for the formula $C_{21}H_{27}ClN_2O$ (358.93): Calculated: C %=70.27, H %=7.58, Cl %=9.89, N %=7.80; Found: C %=70.30, H %=7.55, Cl %=9.90, N %=7.74.

UV: $\lambda_{max}$ = 253 nm ($\epsilon$ = 37950)
262 nm ($\epsilon$ = 38284)
280 nm ($\epsilon$ = 12820)

EXAMPLE 10

3-[2-(Hexahydro-1H-azepinyl)-ethoxyimino]-2,3-dihydro-1H-benz[e]indene

One proceeds as specified in Example 1 except that instead of 2-chloro-N,N-dimethylethylamine hydrochloride 1-(2-chloro-ethyl)-hexahydro-1H-azepine hydrochloride (21.8 g, 0.11 mole) is used.

Yield: 26.42 g (81.3%), m.p.: 46°–47° C.

Hydrochloride (1/1) M.p.: 208°–219° C. (ethanol).

Analysis for the formula $C_{21}H_{27}ClN_2O$ (358.920): Calculated: C %=70.27, H %=7.58, Cl %=9.88, N %=7.81; Found: C %=70.30, H %=7.64, Cl %=9.76, N %=7.80.

UV: $\lambda_{max}$ = 243 nm ($\epsilon$ = 34766)
253 nm ($\epsilon$ = 46986)
261 nm ($\epsilon$ = 41378)

EXAMPLE 11

3-[2-(N-Morpholinoethoxyimino)]-2,3-dihydro-1H-benz[e]indene

One proceeds as specified in Example 1 except that instead of 2-chloro-N,N-dimethylethylamine hydrochloride 4-(2-chloroethyl)-morpholine hydrochloride (20.47 g, 0.11 mole ) is used.

Yield: 24.77 g (79.8%)

Hydrochloride (1/1), m.p.: 197°–216° C.

Analysis for the formula $C_{19}H_{23}ClN_2O_2$ (346.87): Calculated: C %=65.79, H %=6.68, Cl %=10.22, N %=8.08; Found: C %=65.65, H %=6.68, Cl %=10.25, N %=8.15.

UV: $\lambda_{max}$ = 242 nm ($\epsilon$ = 33503)
254 nm ($\epsilon$ = 43875)
262 nm ($\epsilon$ = 38288)

EXAMPLE 12

3-{3-[4-(3-Chlorophenyl)-1-piperazinyl]-propoxyimino}-2,3-dihydro-1H-benz[e]indene One proceeds as specified in Example 1 except that instead of 2-chloro-N,N-dimethylethylamine hydrochloride 1-(3-chloropropyl)-4-(3-chlorophenyl)-piperazine hydrochloride (34.06 g, 0.11 mole) is used.

Yield: 34.46 g (79.4%), m.p: 165°–168° C. (acetone)

Hydrochloride (1/1), m.p.: 198°–203° C. (ethanol)

Analysis for the formula $C_{26}H_{29}Cl_2N_3O$ (470.45): Calculated: C %=66.38, H %=6.22, Cl %=15.07, N %=8.93; Found: C %=66.42, H %=6.18, Cl %=15.11, N %=8.90.

UV: $\lambda_{max}$ = 250 nm ($\epsilon$ = 69748)
260 nm ($\epsilon$ = 41948)

EXAMPLE 13

3-[3-(N-Phthalimido)-propoxyimino]-2,3-dihydro-1H-benz[e]indene 2,3-dihydro-1H-benz[e]indene-3-one oxime (19.72 g, 0.1 mole) is converted into a salt with sodium hydride (4.8 g, 0.1 mole) in dimethylformamide (50% oily dispersion), and the salt thus obtained is reacted with N-(3-bromopropyl)-phthalimide (29.49 g, 0.11 mole) at a temperature of 40° to 50° C. The stirring is continued until the starting oxime cannot be detected in the reaction mixture by thin layer chromatography (Kieselgel 60 F$_{254}$, ethanol:ammonium hydroxide =9:1). The ethanol is added to the mixture, it is diluted with water and the separated product is filtered off.

Yield: 30.29 g (78.8%), m.p.: 161°–163° C. (methylethylketone)

Analysis for the formula C$_{24}$H$_{20}$N$_2$O$_3$ (384.44): Calculated: C %=74.98, H %=5.24, N %=7.29; Found: C %=74.81, H %=5.24, N %=7.44.

UV: $\lambda_{max}$ = 219 nm ($\epsilon$ = 51786)
232 nm ($\epsilon$ = 39809)
240 nm ($\epsilon$ = 37521)

EXAMPLE 14

3-(2-Pyrimidinyloxyimino]-2,3-dihydro-1H-benz[e]indene

One proceeds as specified in Example 13 except that instead of N-(3-bromopropyl)-phthalimide 2-chloropyrimidine (12.60 g, 0.11 mole) is used.

Yield: 21.97 g (79.8%), m.p.: 176°–178° C. (isopropanol).

(E)-2-butanedioate (2/1), m.p.: 190°–195° C. (ethanol).

Analysis for the formula C$_{38}$H$_{30}$N$_6$O$_6$ (666.67): Calculated: C %=68.45, N %=12.61, H %=4.53; Found: C %=68.47, N %=12.58, H %=4.47.

UV: $\lambda_{max}$ = 252 nm ($\epsilon$ = 100438)
262 nm ($\epsilon$ = 93834)

EXAMPLE 15

3-[1-(2,3-Epoxy)-propoxyimino]-2,3-dihydro-1H-benz[e]indene 2,3-Dihydro-1H-benz [e]inden-3-one oxime (19.72 g, 0.1 moles) is converted into a salt with sodium hydroxide (4.8 g, 0.1 mole, 50% oily dispersion in dimethylformamide) and the salt thus obtained is reacted with 1,2-epoxy-3-chloropropane (10.17 g, 0.11 mole) at a temperature of 40° to 50° C. The stirring is continued until the starting oxime cannot be detected in the reaction mixture by thin layer chromatography (Kieselgel 60 F$_{254}$, ethanol:ammonium hydroxide=9:1). Then ethanol is added to the mixture, it is diluted with water and the product thus obtained is extracted with benzene. The solvent is distilled off. The product thus obtained does not require further purification.

Yield: 21.61 g (85.3%), m.p.: 74°–76° C. (n-hexane).

Analysis for the formula C$_{16}$H$_{15}$NO$_2$ (253.304): Calculated: C %=75.87, H %=5.97, N %=5.53; Found: C %=75.79, H %=5.97, N %=5.51.

UV: $\lambda_{max}$ = 244 nm ($\epsilon$ = 32619)
253 nm ($\epsilon$ = 41745)
262 nm ($\epsilon$ = 35645)

EXAMPLE 16

3-{3-[N-(1-Methylethyl)-2-propaneamino]-2-hydroxypropoxyimino}-2,3-dihydro-1H-benz[e]indene a) One proceeds as specified in Example 15.

b) The product obtained according to Example 15 is reacted with N-(1-methylethyl)-2-propaneamine (9.51 g, 0.094 mole) in ethanol (21.65 g, 0.085 mole) at the boiling point of the mixture. The boiling is continued until the starting substance cannot be detected in the reaction mixture by thin layer chromatography (Kieselgel 60, F$_{254}$, ethanol:ammonium hydroxide=9:1). The solvent is distilled off and the product is purified by acidic-alkaline precipitation.

Yield: 26.82 g (89%)

Hydrochloride/water (1/1/1) , m.p.: 179°–186° C. (methylethylketone).

Analysis for the formula C$_{22}$H$_{33}$ClN$_2$O$_3$ (408.98): Calculated: C %=64.61, H %=8.13, Cl %=8.67, N %=6.85; Found: C %=64.57, H %=8.11, Cl %=8.69, N %=6.94.

UV: $\lambda_{max}$ = 242 nm ($\epsilon$ = 33743)
253 nm ($\epsilon$ = 42625)
262 nm ($\epsilon$ = 36938)

EXAMPLE 17

3-[3-(Cyclopropylamino)-2-hydroxypropoxyimino]-2,3-dihydro-1H-benz[e]indene a) One proceeds according to Example 15.

b) One proceeds according to point b) of Example 16 except that instead of N-(1-methylethyl)-2-propaneamine cyclopropylamine (5.37 g, 0. 094 mole) is used.

Yield: 21.37 g (81%), m.p.: 86°–87° C. (n-hexane:ethyl acetate==9:1).

Hydrochloride (1/1) m.p.: 167°–176° C. (isopropanol)

Analysis for the formula C$_{19}$H$_{23}$Cl$_1$N$_2$O$_2$ (346.87): Calculated: C %=65.79, H %=6.68, Cl %=10.22, N %=8.08; Found: C %=65.71, H %=6.65, Cl %=10.22, N %=8.00.

UV: $\lambda_{max}$ = 241 nm ($\epsilon$ = 30179)
252 nm ($\epsilon$ = 37285)
261 nm ($\epsilon$ = 33263)

EXAMPLE 18

3-{3-[4-(2-Hydroxyethyl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-(2-hydroxyethyl)-piperazine (12.24 g, 0,094 mole) is used.

Yield: 24.71 g (75.8%) , m.p.: 104°–107° C.

(Z)-2-butenedioate (1/2), m.p.: 183°–187° C.

Analysis for the formula C$_{30}$H$_{37}$N$_3$O$_{11}$ (615.65): Calculated: C %=58.53, H %=6.06, N %=6.83; Found: C %=58.47, H %=6.10, N %=6.76.

UV: $\lambda_{max}$ = 214 nm ($\epsilon$ = 30800)
254 nm ($\epsilon$ = 39011)
263 nm ($\epsilon$ = 33671)

EXAMPLE 19

3-{3-[4-(2-Methoxyphenyl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-(2-methoxyphenyl)-piperazine (21.15 g, 0.11 mole) is used.

Yield: 37.3 g (83.7%).

Hydrochloride (1/1), m.p.: 187°–190° C.

Analysis for the formula $C_{27}H_{32}ClN_3O_3$ (482.03): Calculated: C %=67.27, H %=6.69, Cl %=7.36, N %=8.72; Found: C %=67.21, H %=6.63, Cl %=7.37, N %=8.68.

UV: $\lambda_{max}$ = 242 nm ($\epsilon$ = 37553)
252 nm ($\epsilon$ = 43057)
260 nm ($\epsilon$ = 36165)

EXAMPLE 20

3-{3-[4-(3-Chlorophenyl)-1-piperazinyl]-2-hydroxypropoxyimino]-2,3-dihydro-1H-benz[e]indene a) One proceeds according to Example 15.

b) One proceeds according to point b) of Example 16 except that instead of N-(1-methylethyl)-2-propaneamine 1-(3-chlorophenyl)-piperazine is used.

Yield: 41.63 g (92.5%), m.p.: 153°–156° C.

(Z)-2-butenedioate (1/1), m.p.: 153°–156° C.

Analysis for the formula $C_{30}H_{32}ClN_3O_6$ (566.07): Calculated: C %=63.65, H %=5.70, Cl %=6.26, N %=7.43; Found: C %=63.69, H %=5.76, Cl %=6.27, N %=7.50.

UV: $\lambda_{max}$ = 244 nm ($\epsilon$ = 45139)
252 nm ($\epsilon$ = 52298)
262 nm ($\epsilon$ = 40837)

EXAMPLE 21

3-(O-Allylcarbamoyl)-oxime-2,3-dihydro-1H-benz[e]indene 2,3-Dihydro-1H-benz[e]-inden-3-one oxime (19.72 g, 0.1 mole) is reacted with allyl isocyanate (9.14 g, 0.11 mole) in dichloromethane at a temperature between 16° C. and 28° C. The stirring is continued until the starting oxime cannot be detected in the reaction mixture by thin layer chromatography.

Yield: 27.67 g (98.7%), m.p.: 161°–166° C. (isopropanol).

Analysis for the formula $C_{17}H_{16}N_2O_2$ (280.33): Calculated: C %=72.84, H %=5.75, N %=10.00; Found: C %=72.82, H %=5,72, N %=9.66.

UV: $\lambda_{max}$ = 243 nm ($\epsilon$ = 36067)
250 nm ($\epsilon$ = 54527)
260 nm ($\epsilon$ = 55017)

EXAMPLE 22

3-(O-Cyclohexylcarbamoyl)-oxime-2,3-dihydro-1H-benz[e]indene

One proceeds as specified in Example 21 except that instead of allyl isocyanate cyclohexyl isocyanate (13.77 g, 0.11 mole) is used.

Yield: 31.91 g (99%), m.p.: 176°–184° C. (isopropanol).

Analysis for the formula $C_{20}H_{22}N_2O_2$ (322.4): Calculated: C %=74.51, H %=6.88, N %=8.69; Found: C %=74.57, H %=6.92, N %=8.67.

UV: $\lambda_{max}$ = 244 nm ($\epsilon$ = 35713)
252 nm ($\epsilon$ = 54914)
260 nm ($\epsilon$ = 54564)

EXAMPLE 23

3-[3-(Cyclohexylamino)-2-hydroxypropoxyimino]-2,3-dihydro-1H-benz[e]indene a) One proceeds according to Example 15.

b) One proceeds according to point b) of Example 16 except that instead of N-(1-methylethyl)-2-propaneamine cyclohexylamine (9.32 g, 0. 094 mole) is used.

Yield: 23.97 g (80%), m.p.: 131°–132° C. (ethanol).

Hydrochloride (1/1), m.p.: 204°–211° C. (ethanol).

Analysis for the formula $C_{22}H_{29}ClN_2O_2$: Calculated: C %=67.94, H %=7.52, Cl %=9.12, N %=7.20; Found: C %=67.75, H %=7.49, Cl %=9.29, N %=7.23.

UV: $\lambda_{max}$ = 244 nm ($\epsilon$ = 31696)
253 nm ($\epsilon$ = 40483)
262 nm ($\epsilon$ = 34411)
282 nm ($\epsilon$ = 13685)
301 nm ($\epsilon$ = 11670)

EXAMPLE 24

3-{3-[4-(4-Chlorophenyl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-[-(4-chlorophenyl)-piperazine (18.49 g, 0.094 mole) is used.

Yield: 32.5 g (85.0%), m.p.: 155°–159° C. (toluene).

Hydrochloride (1/1), m.p.: 199°–211° C. (ethanol).

Analysis for the formula $C_{26}H_{29}Cl_2N_3O_2$ (486.46): Calculated: C %=64.19, H %=6.01, Cl %=14.58, N %=8.64; Found: C %=67.23, H %=6.13, Cl %=14.41, N %=8.99.

UV: $\lambda_{max}$ = 253 nm ($\epsilon$ = 55614)
262 nm ($\epsilon$ = 44063)
280 nm ($\epsilon$ = 15401)
290 nm ($\epsilon$ = 18310)
302 nm ($\epsilon$ = 14460)

EXAMPLE 25

3-{3-[4-(4-Fluorophenyl-methyl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-[4-(fluorophenyl)-methyl]-piperazine (18.26 g, 0.094 mole) is used.

Yield: 34.58 g (91.0%), m.p.:114°–116° C. (ethanol).

Hydrochloride (1/2), m.p.: 207°–213° C. (ethanol).

Analysis for the formula $C_{27}H_{32}FCl_2N_3O_2$ (520.49): Calculated: C %=62.31, H %=6.19, F %=3.65, Cl %=13.62, N %=8.07; Found: C %=61.89, H %=6.42, F %=3.53, Cl %=13.62, N %=8.12.

UV: $\lambda_{max}$ = 242 nm ($\epsilon$ = 31569)
253 nm ($\epsilon$ = 35082)
262 nm ($\epsilon$ = 35370)
290 nm ($\epsilon$ = 15891)
302 nm ($\epsilon$ = 12381)

EXAMPLE 26

3-{3-[4-(4-Chlorophenyl-methyl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-[4-(4-chlorophenyl)-methyl]-piperazine (19.81 g, 0,094 mole) is used.

Yield: 36.48 g, m.p.: 138°–140° C. (ethanol).

Hydrochloride (1/2), m.p.: 207°–214° C. (ethanol).

Analysis for the formula $C_{27}H_{32}Cl_3N_3O_2$ (536.95): Calculated: C %=60.39, H %=6.01, Cl %=19.81, N %=7.83; Found: C %=60.33, H %=6.01, Cl %=19.57, N %=7.83.

UV: $\lambda_{max}$ = 244 nm ($\epsilon$ = 31425)
263 nm ($\epsilon$ = 35082)
281 nm ($\epsilon$ = 13726)
292 nm ($\epsilon$ = 15911)
304 nm ($\epsilon$ = 12727)

EXAMPLE 27

3-{3-[4-(pyrid-9-yl)-1-piperazinyl]-2-hydroxypropoxyimino}-2,3-dihydro-1H-benz[e]indene a) One proceeds according to Example 15.

b) One proceeds according to point b) of Example 16 except that instead of N-(1-methylethyl)-2-propaneamine 1-(2-pyridyl)-piperazine (15.34 g, 0.094 mole) is used.

Yield: 30.80 g (87%), m.p.: 138°–140° C. (ethanol).

Hydrochloride (1/2), m.p.: 172°–175° C. (methanol).

Analysis for the formula $C_{25}H_{30}Cl_2N_4O_2$ (489.46): Calculated: C %=61.35, H %=6.18, Cl %=14.49, N %=11.45; Found: C %=59.58, H %=6.09, Cl %=14.14, N %=11.00.

UV: $\lambda_{max}$ = 242 nm ($\epsilon$ = 44245)
262 nm ($\epsilon$ = 36093)
282 nm ($\epsilon$ = 17853)
290 nm ($\epsilon$ = 19404)
300 nm ($\epsilon$ = 15677)

EXAMPLE 28

3-[(3-Allylamino)-2-hydroxypropoxyimino]-2,3-dihydro-1H-benz[[e]indene a) One proceeds according to Example 15.

b) One proceeds according to point b) of Example 16 except that instead of N-(1-methylethyl)-2-propaneamine allylamine (6.28 g, 0.11 mole) is used.

Yield: 20.84 g (79%), m.p.: 74°–76° C. (n-hexane).

Hydrochloride (1/1), m.p.: 188°–197° C. (ethanol).

Analysis for the formula $C_{19}H_{23}N_2ClO_2$ (346,87): Calculated: C %=65.79, H %=6.68, Cl %=10.22, N %=8.08; Found: C %=65.30, H %=6.73, Cl %=10.20, N %=8.37.

UV: $\lambda_{max}$ = 243 nm ($\epsilon$ = 30817)
253 nm ($\epsilon$ = 38826)
262 nm ($\epsilon$ = 33850)
281 nm ($\epsilon$ = 13200)
290 nm ($\epsilon$ = 15532)
302 nm ($\epsilon$ = 12690)

EXAMPLE 29

(±)-3-(3-Propylamino-2-hydroxypropoxyimino)-2,3-dihydro-1H-benz[e]indene a) One proceeds according to Example 15.

b) The product obtained according to Example 15 (21.61 g, 0. 085 mole) is reacted with propylamine (60.31 g, 1.02 mole) in a closed pressure-tight flask at a temperature of 90°–100° C. (on an oil bath) for 12 hours. The excess of amine is distilled off and the product is purified by acidic-alkaline precipitation.

Yield: 22.04 g (83%), m.p.: 80°–81° C. (n-hexane-ethyl acetate=1:1).

Hydrochloride (1/1), m.p.: 217°–220° C. (ethyl acetate).

Analysis for the formula $C_{19}H_{25}N_2ClO_3$ (348.88): Calculated: C %=65.42, H %=7.22, Cl %=10.16, N %=8.03; Found: C %=65.61, H %=7.13, Cl %=10.18, N %=8.01.

UV: $\lambda_{max}$ = 143 nm ($\epsilon$ = 31155)
253 nm ($\epsilon$ = 38479)
262 nm ($\epsilon$ = 34045)
280 nm ($\epsilon$ = 13477)
290 nm ($\epsilon$ = 15919)
302 nm ($\epsilon$ = 12735)

EXAMPLE 30

3-[3-(1-Methylethylamino)-2-hydroxypropoxyimino]-2,3-dihydro-1H-benz[e]indene a) One proceeds according to Example 15.

b) One proceeds according to point b) of Example 29 except that instead of propylamine isopropylamine (60.31 g, 1.02 mole) is used.

Yield: 22.3 g (84%), m.p.: 107°–108° C. (cyclohexane).

Hydrochloride (1/1), m.p.: 210°–216° C. (ethanol).

Analysis for the formula $C_{19}H_{25}ClN_2O_2$ (348.88): Calculated: C %=65.41, H %=7.22, Cl %=10.16, N %=8.03; Found: C %=65.73, H %=6.98, Cl %=9.92, N %=8.18.

UV: $\lambda_{max}$ = 244 nm ($\epsilon$ = 3400)
252 nm ($\epsilon$ = 41405)
263 nm ($\epsilon$ = 37856)
282 nm ($\epsilon$ = 14375)
291 nm ($\epsilon$ = 16564)
303 nm ($\epsilon$ = 1775)

EXAMPLE 31

3-[3-(1,1-Dimethylethylamino)-2-hydroxypropoxyimino}-2,3-dihydro-1H-benz[e]indene a) One proceeds according to Example 15.

b) One proceeds according to point b) of Example 29 except that instead of propylamine tert-butylamine (74.60 g, 1.02 mole) is used.

Yield: 23.72 g (85.5%), m.p.: 128°–129° C. (isopropanol).

Hydrochloride (1/1), m.p.: 226°–227° C. (isopropanol).

Analysis for the formula $C_{20}H_{27}ClN_2O_2$ (362.92): Calculated: C %=66.19, H %=7.50, Cl %=9.77, N %=7.72; Found: C %=66.57, H %=7.68, Cl %=9.82, N %=7.82.

UV: $\lambda_{max}$ = 244 nm ($\epsilon$ = 31879)
254 nm ($\epsilon$ = 40024)
263 nm ($\epsilon$ = 35600)
281 nm ($\epsilon$ = 16520)
291 nm ($\epsilon$ = 16520)
300 nm ($\epsilon$ = 13264)

EXAMPLE 32

3-{3-[(1,1-Dimethylpropyn-2-yl)-amino]-2-hydroxy-propoxyimino}-2,3-dihydro-1H-benz[e]indene a) One proceeds according to Example 15.

b) One proceeds according to point b) of Example 29 except that instead of propylamine 1,1-dimethylpropyn-2-yl amine (84.8 g, 1.02 mole) is used.

Yield: 23.67 g (82.8%), m.p.: 113°–114° C. (isopropanol).

Hydrochloride (1/1), m.p.: 220°–224° C. (ethanol).

Analysis for the formula $C_{21}H_{25}ClN_2O_2$ (372.90):
Calculated: C %=67.64, H %=6.76, Cl %=9.51, N %=7.51; Found: C %=67.88, H %=6.67, Cl %=9.42, N %=7.40.

UV: $\lambda_{max}$ = 245 nm ($\epsilon$ = 30978)
252 nm ($\epsilon$ = 39669)
263 nm ($\epsilon$ = 34338)
282 nm ($\epsilon$ = 13204)
291 nm ($\epsilon$ = 15094)
303 nm ($\epsilon$ = 12137)

EXAMPLE 33

7-Methyl-3-[1-(2,3-epoxy)-propoxyimino]-2,3-dihydro-1H-benz[e]indene

One proceeds according to Example 15 except that instead of 2,3-dihydro-1H-benz[e]inden-3-one oxime 7-methyl-(2,3-dihydro-1H-benz[e]inden-3-one oxime (21.12 g, 0.1 mole) is used.

Yield: 22.75 g (85%), m.p.: 147°–148° C. (dioxane).

EXAMPLE 34

3-(3-propylamino-2-hydroxypropoxyimino)-7-methyl-2,3-dihydro-1H-benz[e]indene a) One proceeds according to Example 33.

b) The product obtained according to point a) (22.75 g, 0.085 mole) is reacted with propylamine (60.31 g, 1.02 mole) in a closed, pressure-tight flask at a temperature of 90° C. (on an oil bath) for 12 hours. The excess of amine is distilled off and the product is purified by acidic-alkaline precipitation.

Yield: 23.15 g (83.5%), m.p.: 98°–99° C.

Hydrochloride (1/1), m.p.: 213°–215° C.

Analysis for the formula $C_{20}H_{27}N_2ClO_2$ (362.91):
Calculated: C %=66.19, H %=7.50, Cl %=9.77, N %=7.72; Found: C %=66.55, H %=7.56, Cl %=9.85, N %=7.85.

UV: $\lambda_{max}$ = 246 nm ($\epsilon$ = 33579)
253 nm ($\epsilon$ = 41425)
260 nm ($\epsilon$ = 36971)
283 nm ($\epsilon$ = 14124)
292 nm ($\epsilon$ = 16196)
303 nm ($\epsilon$ = 14193)

EXAMPLE 35

3-[3-(1-Methylethylamino)-2-hydroxypropoxyimino]-7-methyl-2,3-dihydro-1H-benz[e]indene a) One proceeds according to Example 33.

b) One proceeds according to point b) of Example 34 except that instead of propylamine isopropylamine (60.31 g, 1.02 mole) is used.

Yield: 23.44 g (84.5%), m.p.: 121°–122° C. (isopropanol).

Hydrochloride (1/1), m.p.: 208°–212° C. (water).

Analysis for the formula $C_{20}H_{27}ClN_2O_2$ (362.91):
Calculated: C %=66.19, H %=7.50, Cl %=9.77, N %=7.72; Found: C %=65.74, H %=7.81, Cl %=9.70, N %=7.50.

UV: $\lambda_{max}$ = 246 nm ($\epsilon$ = 34801)
252 nm ($\epsilon$ = 43800)
260 nm ($\epsilon$ = 37498)
283 nm ($\epsilon$ = 15602)
292 nm ($\epsilon$ = 17101)
302 nm ($\epsilon$ = 14161)

EXAMPLE 36

3-[3-(Cyclopropylamino)-2-hydroxypropoxyimino]-7-methyl-2,3-dihydro-1H-benz[e]indene a) One proceeds according to Example 33.

b) One proceeds according to point b) of Example 34 except that instead of propylamine cyclopropylamine (58.24 g, 1.02 mole) is used.

Yield: 23.44 g (85%), m.p.: 118°–119° C. (isopropanol).

Hydrochloride (1/1), m.p.: 178°–181° C. (isopropanol).

Analysis for the formula $C_{20}H_{25}ClN_2O_2$ (360.89):
Calculated: C %=66.56, H %=6.98, Cl %=9.83, N %=7.76; Found: C %=66.04, H %=6.99, Cl %=9.82, N %=7.60.

UV: $\lambda_{max}$ = 246 nm ($\epsilon$ = 40046)
252 nm ($\epsilon$ = 44110)
262 nm ($\epsilon$ = 38849)
292 nm ($\epsilon$ = 17392)
304 nm ($\epsilon$ = 14685)

EXAMPLE 37

3-{3-[N-(2'-Dimethylaminoethyl)-amino]-2-hydroxypropoxyimino}-7-methyl-2,3-dihydro-1H-benz[e]indene a) One proceeds according to Example 33.

b) One proceeds according to point b) of Example 34 except that instead of propylamine 2-dimethylaminoethylamine (89.91 g, 1.02 mole) is used and the reaction is carried out at a temperature of 140° C.

Yield: 26.36 g (87%), m.p.: 123°–124° C. (isopropanol).

Hydrochloride (1/2), m.p.: 209°–213° C. (isopropanol).

Analysis for the formula $C_{21}H_{32}Cl_2N_3O_2$ (429.43):
Calculated: C %=58.74, H %=7.51, Cl %=16.51, N %=9.79; Found: C %=58.97, H %=7.36, Cl %=16.30, N %=9.30.

UV: $\lambda_{max}$ = 254 nm ($\epsilon$ = 42210)
261 nm ($\epsilon$ = 36088)
293 nm ($\epsilon$ = 13708)
303 nm ($\epsilon$ = 12646)

EXAMPLE 38

3-{3-[N-3'-Dimethylaminopropyl)-amino]-2-hydroxy-propoxyimino}-7-methyl-2,3-dihydro-1H-benz[e]indene a) One proceeds according to Example 33.

b) One proceeds according to point b) of Example 34 except that instead of propylamine 3-dimethylamino-1-propylamine (104.22 g, 1.02 mole) is used and the reaction is carried out at 150° C.

Yield: 26.92 g (85.5%), m.p.: 123°–124° C. (isopropanol).

Hydrochloride (1/2), m.p.: 209°–213° C. (ethanol).

Analysis for the formula $C_{22}H_{34}Cl_2N_3O_2$ (443.45): Calculated: C %=58.74, H %=7.51, Cl %=16.51, N %=9.79; Found: C %=58.97, H %=7.36, Cl %=16.30, N %=9.30.

UV: $\lambda_{max}$ = 253 nm ($\epsilon$ = 43466)
260 nm ($\epsilon$ = 34894)
291 nm ($\epsilon$ = 15187)
302 nm ($\epsilon$ = 12672)

EXAMPLE 39

3-{3-[N-(2-Pyridiyl)-piperazin-1-yl]-2-hydroxypropoxyimino}-7-methyl-2,3-dihydro-1H-benz[e]indene a) One proceeds according to Example 33.

b) The compound obtained according to Example 33 is further reacted according to point b) of Example 27.

Yield: 31.1 g (84.9%), m.p.: 149°–150° C. (acetonitrile).

Hydrochloride (1/2), m.p.: 177°–182° C. (ethanol).

Analysis for the formula $C_{26}H_{32}Cl_2N_4O_2$ (503.49): Calculated: C %=62.02, H %=6.41, Cl %=14.08, N %=11.13; Found: C %=64.10, H %=6.69, Cl %=13.63, N %=10.89.

UV: $\lambda_{max}$ = 242 nm ($\epsilon$ = 44821)
252 nm ($\epsilon$ = 45555)
260 nm ($\epsilon$ = 38740)
283 nm ($\epsilon$ = 17037)
291 nm ($\epsilon$ = 20182)
301 nm ($\epsilon$ = 16513)

EXAMPLE 40

Tablet comprising 25 mg of active ingredient
The composition of one tablet is as follows:

| | |
|---|---|
| active ingredient | 25.0 mg |
| corn starch | 97.0 mg |
| polyvinyl-pyrrolidone | 175.0 mg |
| magnesium stearate | 3.0 mg |
| | 300.0 mg |

The tablet is prepared as follows:

The active ingredient and the corn starch are admixed, then wetted with an aqueous polyvinyl-pyrrolidone solution of 10 to 15% by weight strength and the mixture is granuled, then dried at a temperature of 40° to 50° C. The dry granules are rubbed through a sieve, mixed with talc and magnesium stearate and tablets are prepared from the mixture.

The weight of one tablet is 300.0 mg.

EXAMPLE 41

Tablet comprising 250 mg of active ingredient
The composition of one tablet is as follows:

| | |
|---|---|
| active ingredient | 250.0 mg |
| lactose | 270.0 mg |
| corn starch | 75.0 mg |
| magnesium stearate | 5.0 mg |
| | 600.0 mg |

The active ingredient, the lactose and the corn starch are wetted and mixed, granulated and dried at a temperature of 40 to ° 50° C. The dry granules are rubbed through a sieve as described hereinabove, mixed with magnesium stearate and talc, then tablets are formed.

The weight of one tablet is 600.0 mg.

EXAMPLE 42

Dragées comprising 25 mg of active ingredient
The composition of one dragée core is as follows:

| | |
|---|---|
| active ingredient | 25.0 mg |
| corn starch | 245.0 mg |
| talc | 18.0 mg |
| gelatin | 8.0 |
| magnesium stearate | 4.0 mg |
| | 300.0 mg |

The tablet is prepared as follows:

The active ingredient and the corn starch are mixed, wetted with an aqueous gelatin solution of 10% by weight, granules are formed from the wet mixture, then the granules are dried at a temperature of 40° to 50° C. The dry granules are rubbed through a sieve, homogenized with talc and magnesium stearate and dragée cores of 300.0 mg are compressed from the mixture.

EXAMPLE 43

Dragées comprising 50.0 mg of active ingredient
The composition of one dragée core is as follows:

| | |
|---|---|
| active ingredient | 50.0 mg |
| lactose | 97.0 mg |
| polyvinyl-pyrrolidone | 2.0 mg |
| magnesium stearate | 1.0 mg |

The granules are prepared as described hereinabove.
The weight of the dragée core is 150.0 mg.

The dragée cores are coated with a layer containing sugar and talc in a manner known per se. The dragées thus obtained are painted with non-toxic food paint to the desired colour and polished with bee-wax.

EXAMPLE 44

Gelatin capsule comprising 5.0 mg of active ingredient
The composition of one gelatin capsule is as follows:

| | |
|---|---|
| active ingredient | 5.0 mg |
| corn starch | 40.0 mg |
| Aerosil | 3.0 mg |

| | |
|---|---|
| magnesium stearate | 2.0 mg |
| | 50.0 mg |

The ingredients are homogenized and filled into gelatin capsules of suitable size.

EXAMPLE 45

Gelatin capsule comprising 25.0 mg of active ingredient

The composition of one gelatin capsule is as follows:

| | |
|---|---|
| active ingredient | 25.0 mg |
| corn starch | 265.0 mg |
| Aerosil | 6.0 mg |
| magnesium stearate | 4.0 mg |
| | 300.0 mg |

The ingredients are homogenized and filled into gelatin capsules of suitable size.

EXAMPLE 46

Gelatin capsule comprising 50.0 mg of active ingredient

The composition of one gelatin capsule is as follows:

| | |
|---|---|
| active ingredient | 50.0 mg |
| lactose | 90.0 mg |
| Aerosil | 6.0 mg |
| magnesium stearate | 4.0 mg |
| | 150.0 mg |

The ingredients are homogenized and filled into gelatin capsules of suitable size.

EXAMPLE 47

Gelatin capsule comprising 250.0 mg of active ingredient

The composition of one gelatin capsule is as follows:

| | |
|---|---|
| active ingredient | 250.0 mg |
| lactose | 148.0 mg |
| magnesium stearate | 2.0 mg |
| | 400.0 mg |

The ingredients are homogenized and filled into gelatin capsules of suitable size.

EXAMPLE 48

Injection comprising 25.0 mg of active ingredient
The composition of one ampoule is as follows:

| | |
|---|---|
| active ingredient | 25.0 mg |
| sodium chloride | 5.0 mg | dissolved in 5 cm³ of twice-distilled water.

The active ingredient and sodium chloride are dissolved in the necessary amount of twice-distilled water suitable for making injections. The solution is filtered, filled into ampoules and sterilized.

EXAMPLE 49

Injection comprising 50.0 mg of active ingredient
The composition of one ampoule is as follows:

| | |
|---|---|
| active ingredient | 50.0 mg |
| sodium chloride | 10.0 mg |

The active ingredient and the sodium chloride are dissolved in the necessary amount of twice-distilled water, then filled into ampoules under sterile conditions.

EXAMPLE 50

Suppository comprising 250 mg of active ingredient
The composition of one suppository is as follows:

| | |
|---|---|
| active ingredient | 250.0 mg |
| fatty acid glyceride | 750.0 mg |

The fatty acid glyceride is melted, the active ingredient is homogenized, then poured into a mould. One suppository weights 1000.0 mg and comprises 250.0 mg of active ingredient.

EXAMPLE 51

Drop comprising 5% by weight of active ingredient

| | |
|---|---|
| active ingredient | 25.0 mg |
| sorbitol | 340.0 mg |
| polyethylene glycol | 100.0 mg |
| citric acid | 1.0 mg |
| sodium citrate | 3.0 mg |
| ion-free water | 30.0 cm³ |
| flavourant | 1.0 mg |
| | 500.0 mg |

The sorbitol, the active ingredient, citric acid and sodium citrate are dissolved in the aqueous solution of polyethylene glycol, then after dissolution of the solid material the flavourant is added. The solution is filtered and filled into flasks supplied with a drop-dispenser.

What we claim is:

1. A benz(e)indene of the formula

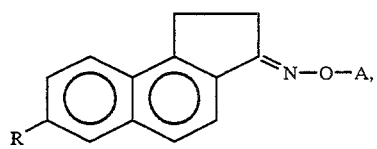

(I)

wherein

A represents a group of the formula alk-NR¹R² wherein alk represents a $C_{2-7}$ alkylene group optionally carrying a hydroxy substituent, $R^1$ and $R^2$ are independently hydrogen, $C_{1-7}$ alkyl, $C_{2-7}$ alkenyl, $C_{2-7}$ alkynyl, mono($C_{1-7}$)alkylamino($C_{1-7}$)alkyl, di($C_{1-7}$)alkylamino($C_{1-7}$)alkyl or $C_{3-3}$cycloalkyl; or $R^1$ and $R^2$ together with the nitrogen atom to which they are attached form a 4 to 7 membered ring, optionally comprising an oxygen atom or a further nitrogen atom, which latter may carry a phenyl, benzyl, pyridyl, pyrimidinyl or $C_{1-3}$ alkyl substituent which substituents may, in turn, bear a hydroxy or methoxy group or a halogen atom or a halophenyl group; or R¹ and R² together with the nitrogen atom to which they are attached form a phthalimido group; or A represents pyrimidino, 2,3-epoxypropyl or a group of the formula —C(O)NHR³, wherein R³ stands for $C_{1-7}$ alkyl, $C_{2-7}$ alkenyl or $C_{3-8}$ cycloalkyl; and R denotes hydrogen or $C_{1-7}$ alkyl, stereoisomers and optionally active isomers and the possible mixtures thereof, and further acid addition salts of these compounds.

2. 3-(3-(cyclopropylamino)-2-hydroxypropoxyimino)-2,3-dihydro-1H-benz(e) indene and acid addition salts thereof.

3. A pharmaceutical composition comprising as active ingredient at least one compound of the formula (I), wherein A and R are as defined in claim 1, or a pharmaceutically acceptable acid addition salt thereof, in admixture with suitable inert solid or liquid pharmaceutical carriers.

* * * * *